(12) United States Patent
Yu (10) Patent No.: US 9,241,722 B2
(45) Date of Patent: Jan. 26, 2016

(54) SURGICAL PIN GUIDE AND METHODS OF USE

(71) Applicant: Warsaw Orthopedic, Inc., Warsaw, IN (US)

(72) Inventor: Kidong Yu, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 485 days.

(21) Appl. No.: 13/647,201

(22) Filed: Oct. 8, 2012

(65) Prior Publication Data

US 2014/0100580 A1   Apr. 10, 2014

(51) Int. Cl.
*A61B 17/04* (2006.01)
*A61B 17/16* (2006.01)
*A61B 17/34* (2006.01)
*A61B 17/00* (2006.01)

(52) U.S. Cl.
CPC ......... *A61B 17/1697* (2013.01); *A61B 17/3403* (2013.01); *A61B 17/3468* (2013.01); *A61B 2017/00438* (2013.01)

(58) Field of Classification Search
CPC ........... A61B 17/0482; A61B 17/0483; A61B 17/0469; A61B 2017/00438
See application file for complete search history.

(56) References Cited

U.S. PATENT DOCUMENTS

| 4,873,998 | A | | 10/1989 | Joyner | |
|---|---|---|---|---|---|
| 5,220,690 | A | * | 6/1993 | Hoos | 2/21 |
| 5,688,181 | A | * | 11/1997 | Albert | 473/61 |
| 5,925,064 | A | * | 7/1999 | Meyers et al. | 606/205 |
| 6,332,888 | B1 | | 12/2001 | Levy et al. | |
| 6,500,188 | B2 | | 12/2002 | Harper et al. | |
| 8,465,503 | B2 | * | 6/2013 | Gaynor et al. | 606/144 |
| 2004/0193211 | A1 | * | 9/2004 | Voegele et al. | 606/205 |
| 2008/0243178 | A1 | * | 10/2008 | Oren et al. | 606/210 |
| 2011/0092987 | A1 | * | 4/2011 | Gaynor et al. | 606/139 |

\* cited by examiner

*Primary Examiner* — Anu Ramana (57) ABSTRACT

A surgical guide is disclosed and methods of use are disclosed. The surgical guide is adapted to receive a surgeon's finger for dissecting to a target site. The surgical guide comprises a first component defining a channel and comprising a palpating portion and a non-palpating portion disposed on an opposing side from the palpating portion. The surgical guide further comprises a second component engaged with the first component and defining a guide channel extending therethrough. The guide channel is adapted to receive a guide pin suitable for insertion to the target site such that the guide pin is carried adjacent the non-palpating portion of the first component.

13 Claims, 7 Drawing Sheets

SURGICAL PIN GUIDE AND METHODS OF USE

TECHNICAL FIELD

The present disclosure generally relates to medical devices, systems and methods for the treatment of musculoskeletal disorders, and more particularly, to a surgical pin guide system and method for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants and, in some cases, the placement of interbody implants via surgical pathways established by guide wires or guide pins placed in specific anatomical structures. For example, such guide pins may serve as waypoints for guiding a series of sequential dilation instruments over the guide pin and to a selected surgical site. This disclosure describes an improvement in these technologies.

SUMMARY

Accordingly, a palpating surgical guide and method are disclosed. In one embodiment, a surgical guide is provided. The surgical guide includes a first component comprising a palpating portion and a non-palpating portion disposed on an opposing side from the palpating portion. The first component defines a channel extending therethrough. The surgical guide also comprises a second component engaged with the first component at the non-palpating portion. The second component defines a guide channel extending therethrough, wherein the guide channel is adapted to receive a guide member. In an exemplary embodiment, the channel of the first component is adapted to receive a finger of a surgeon such that the finger extends outward from a distal end of the first component and such that the finger is disposed between the palpating portion and the non-palpating portion of the first component.

In one embodiment, a surgical guide system is provided for manually dissecting between a first anatomical structure and a second anatomical structure. The surgical guide system comprises a first component including a palpating portion and an opposing. The first component defines a channel adapted to receive a finger of a surgeon such that the finger extends outward from a distal end of the first component and such that the finger is disposed between the palpating portion and the non-palpating portion. Therefore, the palpating portion is disposed adjacent the first anatomical structure and the non-palpating portion is disposed adjacent the second anatomical structure. The surgical guide system further comprises a second component operably engaged with the first component at the non-palpating portion. The second component defines a guide channel extending therethrough. The surgical guide system further comprises a guide member slidably disposed in the guide channel. The guide member (such as a guide pin, for example) is adapted to be placed at a target site between the first anatomical structure and the second anatomical structure while the surgeon maintains the palpating portion adjacent at least one of the first and second anatomical structures, thereby preventing the guide member from inadvertently contacting the anatomical structures when being introduced to the target site.

In one embodiment, a method for manually dissecting to a target site located between a first anatomical structure and a second anatomical structure is provided. The method comprises placing the surgical guide on a finger and dissecting a plurality of tissues adjacent the first and second anatomical structures using the finger and surgical guide. The method further comprises palpating the first anatomical structure with the finger such that the palpating portion of the first component of the surgical guide is adjacent the first anatomical structure; and palpating the second anatomical structure with the finger such that the palpating portion of the first component of the surgical guide is adjacent the second anatomical structure and such that a distal end of the second component of the surgical guide is adjacent the target site. The method may further comprise placing a guide pin through the guide channel of the second component of the surgical guide until the guide pin emerges from the distal end and into the target site. The method may further comprise moving the finger and surgical guide distally away from the target site and leaving the guide pin placed at the target site between the first and second anatomical structures, leaving a surgical pathway (via the guide pin) to the target site by introducing one or more dilators over the guide pin.

BRIEF DESCRIPTION OF THE DRAWINGS

The present disclosure will become more readily apparent from the specific description accompanied by the following drawings, in which.

DETAILED DESCRIPTION

The exemplary embodiments of a surgical guide, surgical guide system and related methods of use disclosed herein are discussed in terms of medical devices for the treatment of musculoskeletal disorders and more particularly, in terms of a surgical guide donned by a surgeon and related methods for treating a vertebral column. It is envisioned that the disclosed surgical guide may provide, for example, a surgical guide that may allow a surgeon to palpate sensitive anatomical structures (such as the descending aorta and/or psoas muscle) while simultaneously introducing a guide pin to a target site located in close proximity to said sensitive anatomical structures. In one embodiment, the surgical guide includes an open palpating portion on one side (allowing the surgeon to place a gloved finger directly on a blood vessel, for example) and includes a guide channel opposite the palpating portion such that the surgeon's finger maintains a positive distance between the palpating portion and the guide pin (which may have sharp points designed for piercing the target site).

The various embodiments described herein may be especially useful in establishing oblique surgical pathways for open, mini-open, or minimally-invasive spinal surgeries in the lower lumbar (L2-L5) or sacro-lumbar (L5-S1) regions where a surgeon may wish to place guide pins in spinal structures at an anterior-oblique angle between especially sensitive anatomical structures that may include, but are not limited to: the blood vessels of the lower abdomen, the peritoneum wall, ureter, and the lateral psoas muscle. For example, a retroperitoneal oblique approach to the L2-L5 disc spaces or to the L5-S1 disc space may be an ideal surgical technique for avoiding the muscle splitting and/or tearing inherent in posterior or direct lateral (trans-psoas) approaches. An "oblique-lateral" technique may be attempted with the patient positioned on their side, using a surgical approach that takes place just anterior to the psoas muscle located laterally along the vertebral column. This approach also takes place slightly posterior of the great vessels that lie almost directly in front of the spinal column at the lower levels of the spine. Dissection and manipulation of these vessels may be time-consuming and difficult. The various embodiments described herein allow a surgeon to more safely and efficiently place surgical guide wires or guide pins in a target site along the "oblique-lateral" surgical pathway between the psoas and the anteriorly-located great vessels.

Figure 1:
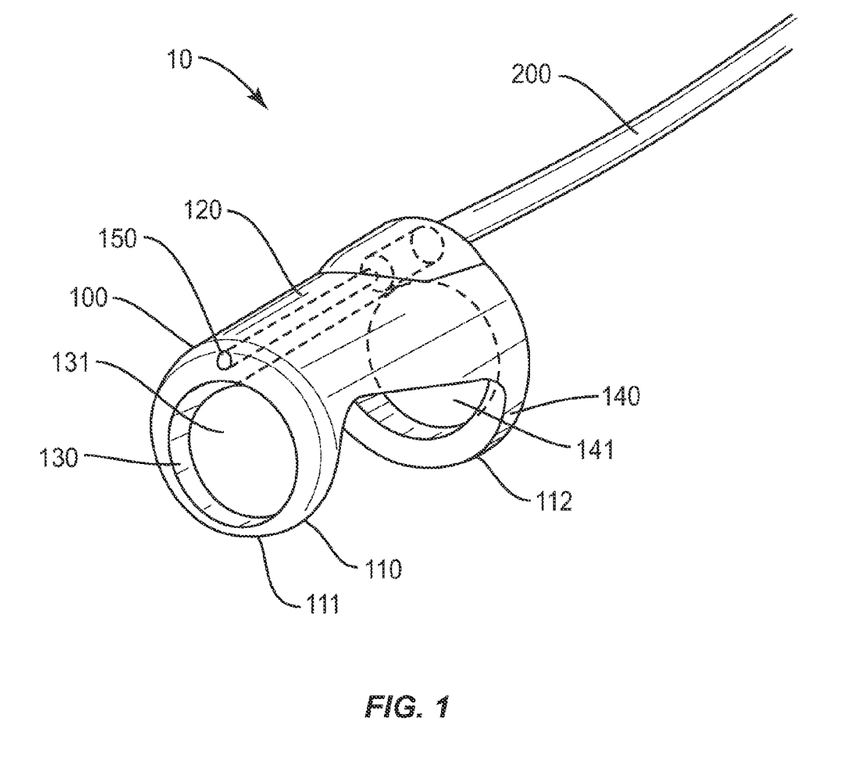
FIG. 1 is a perspective view of a surgical guide, according to one embodiment.

Referring first to FIG. 1, a surgical guide 10 is shown having a first component 100 and a second component 200. The first component 100 comprises a palpating portion 110 and a non-palpating portion 120 disposed on an opposing side from the palpating portion 110. The first component 100 also defines a channel 131, 141 extending through the first component 100 such that a surgeon's finger F may be placed through the channel 131, 141 as shown generally in FIG. 2. Thus, the surgical guide 10 may be donned by a surgeon and used for manually dissecting between a first anatomical structure P (such as the psoas muscle depicted in FIG. 3) and a second anatomical structure (such as the great vessels V depicted in FIG. 3).

Figure 2:
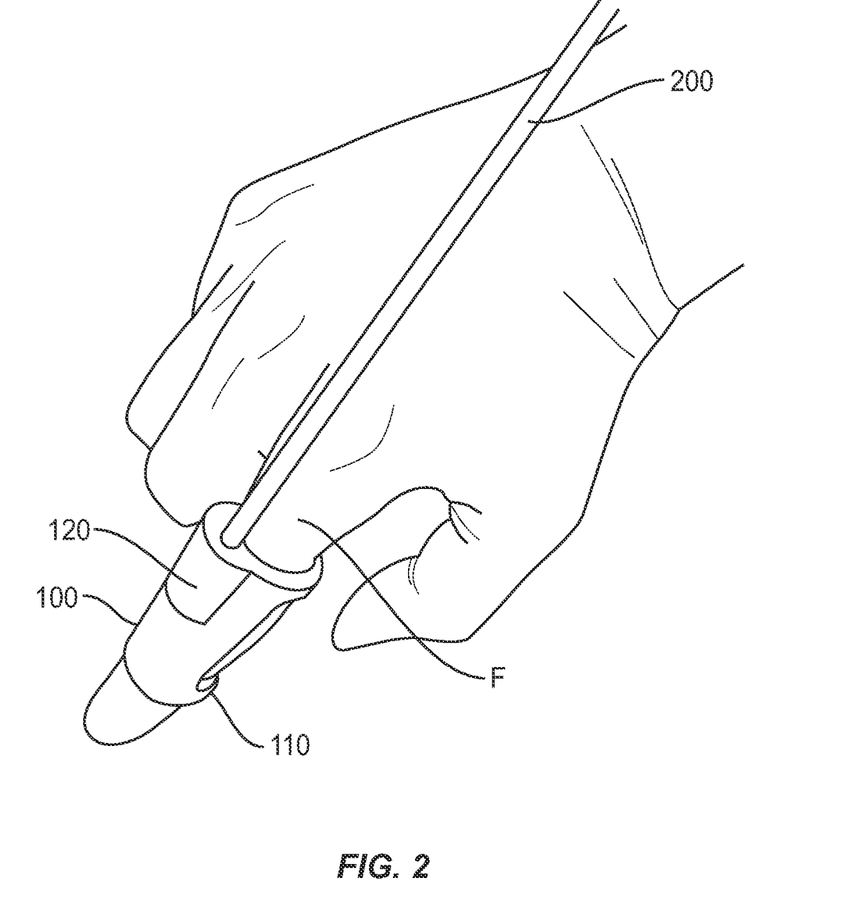
FIG. 2 is a perspective view of a surgical guide placed on a surgeon's finger, according to one embodiment.
Figure 3:
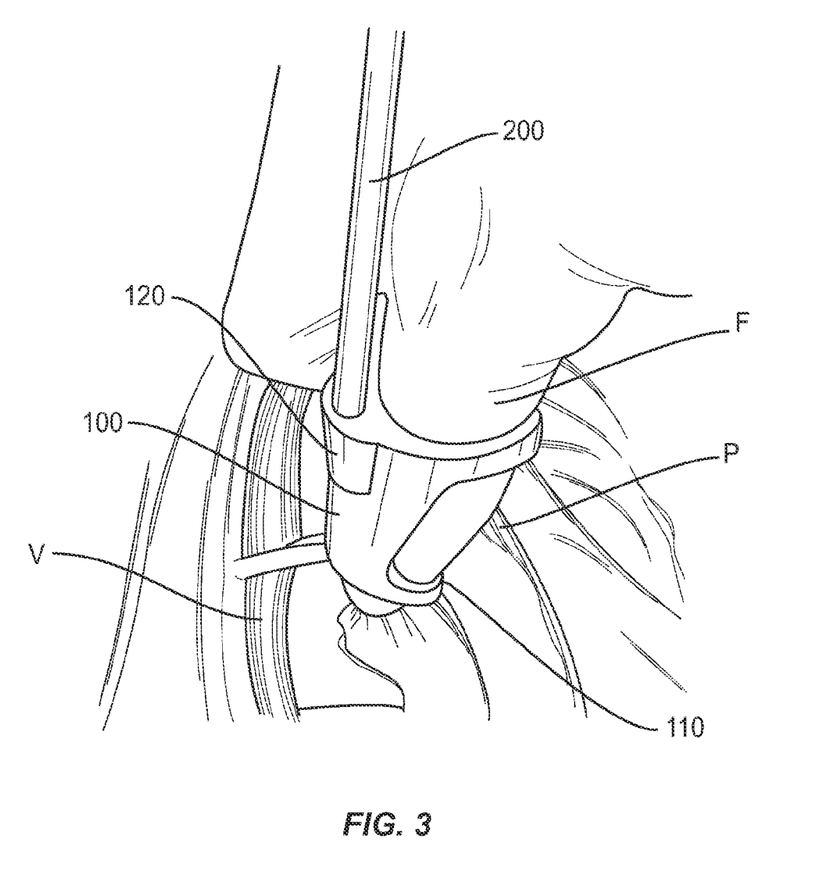
FIG. 3 is a perspective view of a surgical guide placed on a surgeon's finger palpating the psoas muscle, according to one embodiment.
Figure 4:
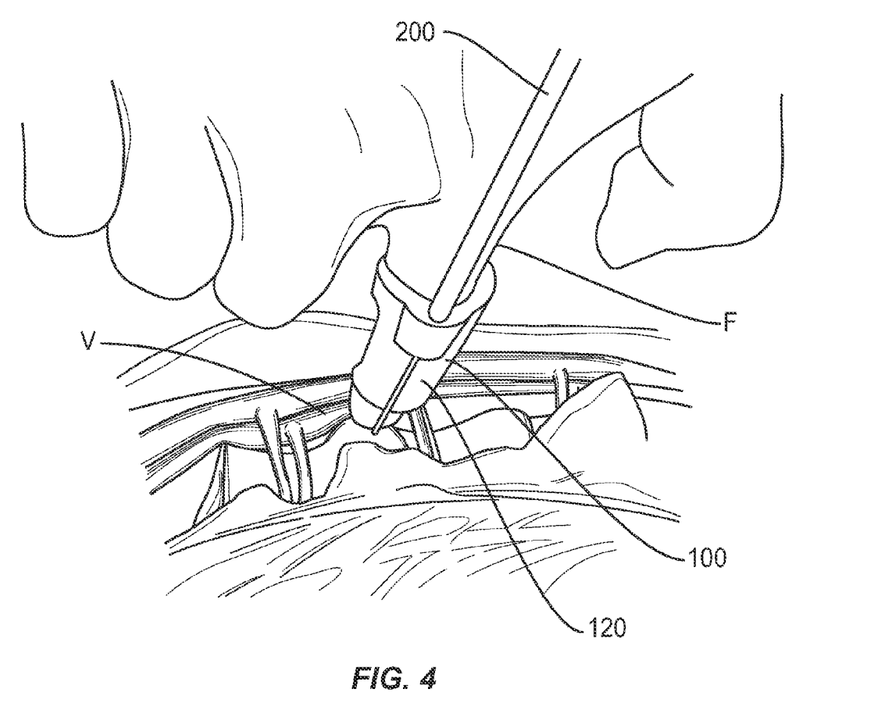
FIG. 4 is a perspective view of a surgical guide placed on a surgeon's finger palpating a blood vessel, according to one embodiment.

As shown in FIG. 1, the first component 100 may comprise a cylindrical tube sized and shaped to fit and/or be donned by a surgeon on his/her finger F (see FIG. 2) for manual dissection of tissue to a surgical target site (see FIGS. 3 and 4). Furthermore, in some embodiments, the palpating portion 110 of the first component 100 may define an opening therein, such that a gloved finger F of the surgeon may be at least partially exposed along a portion of the palpating portion 110 and such that the surgeon may directly palpate sensitive anatomical structures (such as the psoas P and/or vessels V as shown in FIGS. 3 and 4, respectively) during the dissection process to the target site. In some embodiments, the first component 100 comprises distal and proximal ends 130, 140 wherein the palpating portion 110 further comprises a first ring 111 (defining opening 131) disposed at the distal end and a second ring 112 (defining opening 141) disposed at the proximal end. A palpating opening (see palpating portion 110 in FIG. 2, for example) is therefore defined between the first ring 111 and the second ring 112 such that the surgeon's finger F is exposed for direct palpation of tissues or anatomical structures on the palpating portion 110 of the first component 100. As shown generally in FIG. 2, the first component 100 may comprise a tapered cylindrical tube comprising a distal end 130 and a proximal end 140 wherein the first component 100 tapers from a larger diameter at the proximal end 140 or a smaller diameter (relative to the larger diameter) at the distal end 130.

Referring again to FIG. 1, the surgical guide 10 further comprises a second component 200 operably engaged with the first component 100 at the non-palpating portion 120. The second component 200 may comprise a cylindrical tube as shown generally in FIG. 2 defining a guide channel therethrough wherein the guide channel has a cross-section that is sized and adapted to pass a guide member 300 therethrough (see FIG. 5, for example). The second component 200 may be integrally formed with the first component 100 or placed in a bore hole defined in the first component 100. In other embodiments, the second component 200 may be permanently or releasably attached to the first component using a variety of methods and structures that may include, but are not limited to: adhesives, fasteners and/or clips. As shown in FIG. 2, the second component 200 may be integrally formed with the first component 100 along a length of the non-palpating portion 120 of the first component 100.

Figure 5:
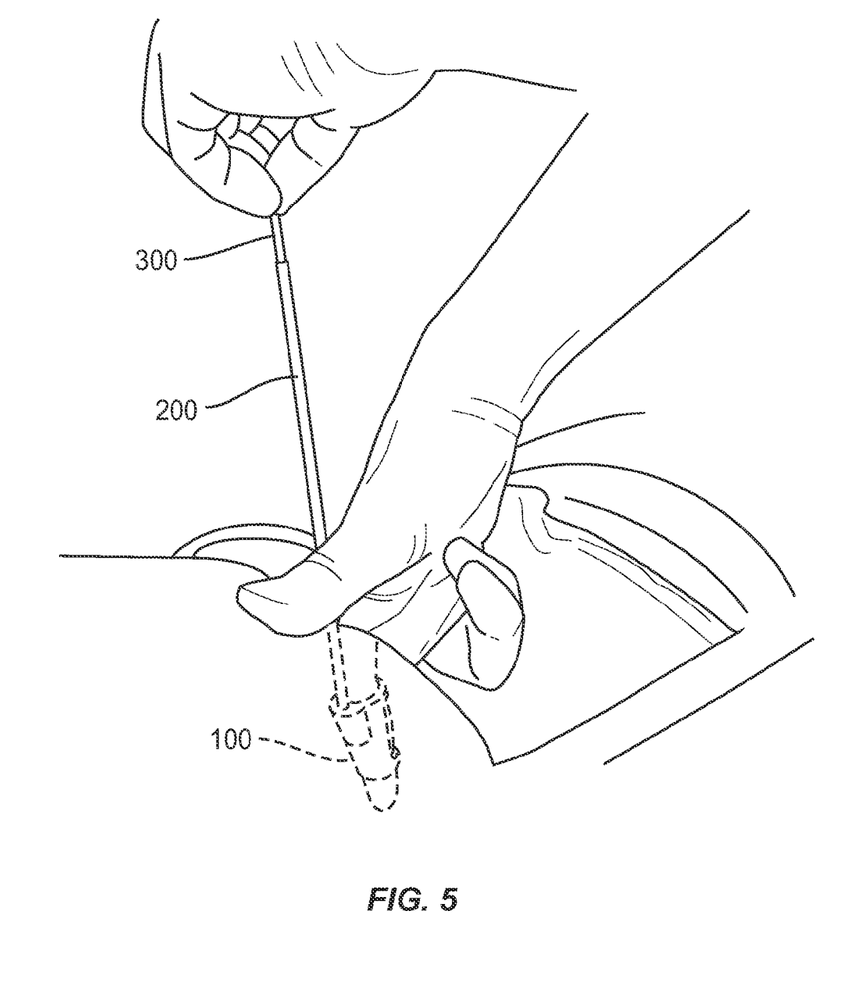
FIG. 5 is a perspective view of a guide pin being placed through a surgical guide, according to one embodiment.

As shown in FIG. 5, the surgical guide 10 may be part of a surgical guide system comprising a guide member 300 (such as a piercing guide wire, "K-wire" and/or guide pin) that is slidably disposed in a guide channel defined in the second component 200. The guide member 300 may comprise a guide pin having a sharpened distal end configured for piercing a surgical target site. For example, the guide member 300 may be placed at an oblique-lateral position in a vertebral body and/or in an intervertebral disc to establish a target site for spinal surgery along an oblique-lateral surgical pathway between the first anatomical structure and the second anatomical structure. The first and second anatomical structures may consist of one or more of the great vessels V and the psoas muscle P (as shown generally in FIGS. 3 and 4).

FIG. 2 shows an exemplary embodiment of the surgical guide comprising first and second components 100, 200 placed on the surgeon's finger F such that the finger F extends outward from a distal end 130 of the first component 100 and such that the finger F is disposed between the palpating portion 110 and the non-palpating portion 120 of the first component 100. Therefore, as shown in FIG. 3, after manually dissecting the tissues leading to a surgical target site, the palpating portion 110 may be initially disposed adjacent a first anatomical structure (such as the psoas muscle P) and the non-palpating portion may be disposed adjacent a second anatomical structure (such as the great vessels V). In this step, a surgeon may positively palpate and identify the psoas muscle P, using the palpating portion 110.

FIG. 4 shows a palpation of the great vessels V wherein the palpating portion 110 of the first component 100 is disposed adjacent a first anatomical structure (in this instance, the great vessels V). In FIG. 4, the non-palpating portion 120 (and the second component 200 carried thereby) is disposed adjacent the second anatomical structure (the psoas P, in this example) such that the second component 200 (and the guide element 300 (see FIG. 5) placed through the second component 200) is position away from the great vessels V and physically separated from the palpated vessels V by the surgeon's finger F while the guide element 300 is advanced through the second component 200 and to the surgical target site.

A method for manually dissecting to a surgical target site located between first and second anatomical structures (such as the psoas P and great vessels V) is also disclosed. The various steps of an exemplary method embodiment are shown sequentially in FIGS. 1-7. The method comprises placing a surgical guide on a finger F (see FIG. 2, for example). The surgical guide 10 may comprise one or more of the various surgical guide and surgical guide system embodiments disclosed herein.

The method further comprises dissecting a plurality of tissues adjacent the first and second anatomical structures using the finger F and surgical guide 10. The result of the dissection step is shown generally in FIGS. 3 and 4 wherein the distal tip of the finger is used to palpate one or more of the anatomical structures (such as the psoas P and/or the great vessels V located anterior to the spinal column).

As shown generally in FIG. 3, the method further comprises palpating the first anatomical structure (such as the psoas P and/or the great vessels V located anterior to the spinal column) with the finger F such that the palpating portion 110 of the first component 100 of the surgical guide 10 is adjacent the first anatomical structure. In some method embodiments, the first palpating step may comprise palpating the psoas P muscle to ascertain its position relative to the adjacent second anatomical structure (such as the great vessels V) prior to the insertion of a guide member 300 through the second component 200 of the surgical guide 10. In this way, a surgeon may preliminarily locate the psoas P and vessels V prior to the second palpating step (shown generally in FIG. 4) which may comprise palpating the vessels V directly with the palpating portion 110.

FIG. 4 depicts another method step comprising palpating a second anatomical structure (such as the great vessels V located anterior to the spinal column at levels L2-L5, for example). The second palpating step shown in FIG. 4 may comprise palpating the vessels V with the finger F such that the palpating portion 110 of the first component 100 of the surgical guide 10 is adjacent the anatomical structure and such that a distal end 150 of the second component 200 is immediately adjacent a target surgical site. In this step (FIG. 4, for example) the surgeon may maintain positive contact with the most sensitive anatomical structure (the vessels V, for example) prior to inserting the sharpened guide element 300 into the surgical site via the second component 200 (see FIG. 5). In this step, the structure of the surgical guide 10 and the placement of the finger F may ensure that the guide element 300 is safely inserted to a selected surgical site without penetrating one or more of the sensitive anatomical structures surrounding the surgical target site.

Figure 6:
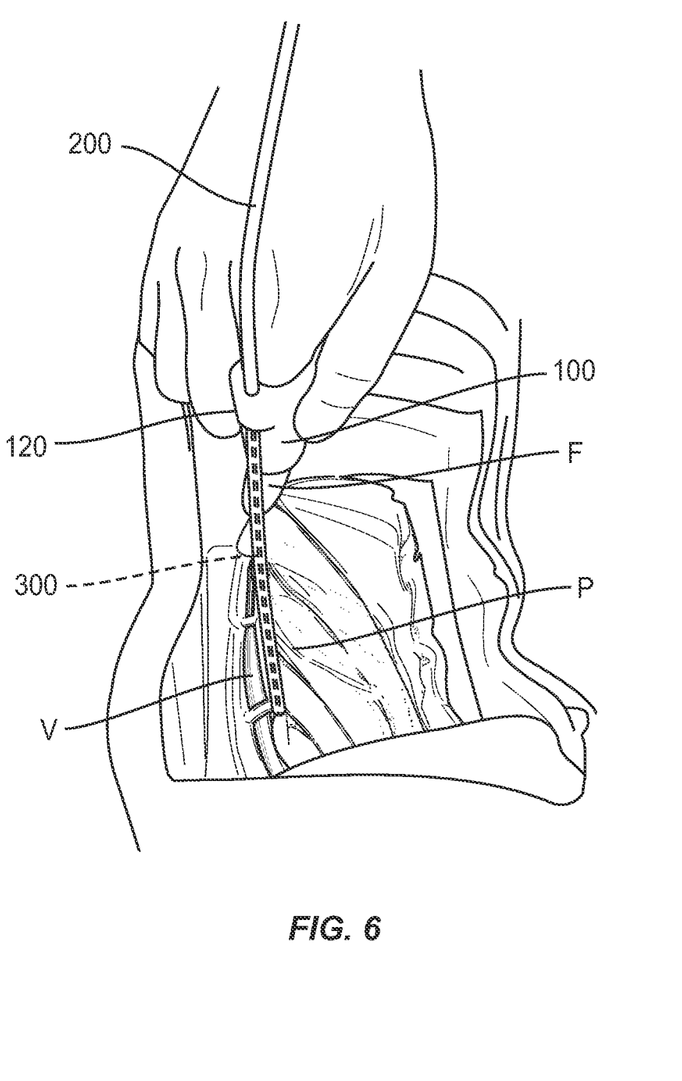
FIG. 6 is a perspective view of a surgeon's finger and an associated surgical guide being removed from the guide pin, according to one embodiment.
Figure 7:
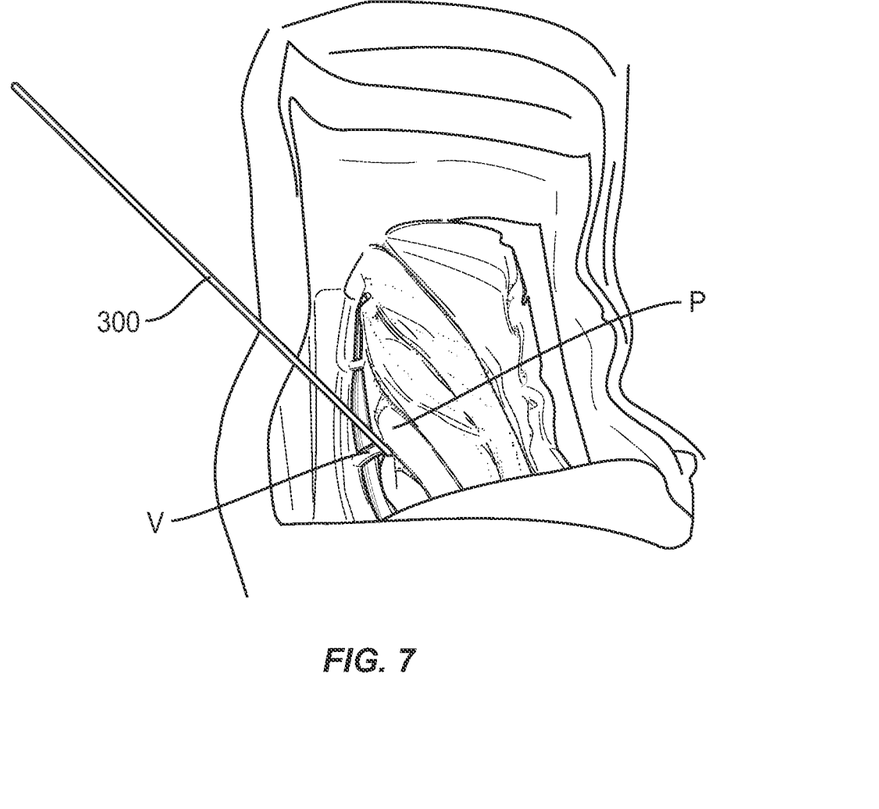
FIG. 7 is a perspective view of a guide pin's final placement using a surgical guide and associated method, according to one embodiment.

As shown in FIG. 6, the method may further comprise the step of placing a guide pin 300 through the guide channel defined in the second component 200 until the guide pin 300 emerges from the distal end 150 and into the target site. As shown in FIG. 7, the method may further comprise a step of moving the finger F and surgical guide 10 distally away from the target site (and generally out of the surgical field) and leaving the guide pin 300 placed at the target site between the first and second anatomical structures (P, V, for example).

Once placed, the guide pin 300 may be used to place a variety of cannulated surgical instruments over the guide pin 300 and directly to the surgical site. Such instruments may include, but are not limited to: surgical retractors, sequential dilation tubes, drill taps, drill tips, surgical portals, needles, implant insertion devices, and/or other instruments configured to be placed and directed via a guide pin or guide wire.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical guide comprising:
  a first component comprising a distal end and a proximal end and comprising a palpating portion and a non-palpating portion disposed on an opposing side from the palpating portion, the palpating portion comprising a first ring defining the distal end, a second ring defining the proximal end, and an opening defined along the palpating portion between the first and second rings, the first component defining a channel extending therethrough; and
  a second component attached to the non-palpating portion of the first component, the second component defining a guide channel extending therethrough, the guide channel adapted to receive a guide member therethrough;
  wherein the channel of the first component is adapted to receive a finger of a surgeon such that the finger extends outward from the distal end of the first component and such that the finger is disposed between the palpating portion and the non-palpating portion of the first component.

2. A surgical guide as recited in claim 1 wherein the first component comprises a cylindrical tube.

3. A surgical guide as recited in claim 1 wherein the second component comprises a cylindrical tube.

4. A surgical guide as recited in claim 1 wherein the second component is attached to the non-palpating portion of the first component along a length of the first component between the distal end and the proximal end.

5. A surgical guide as recited in claim 1 wherein the first component comprises a tapered cylindrical tube comprising a distal end and a proximal end and wherein the first component tapers from a larger diameter at the proximal end to a smaller diameter at the distal end.

6. A surgical guide as recited in claim 1 wherein the second component is integrally formed with the first component along a length of the non-palpating portion of the first component.

7. A surgical guide system for manually dissecting between a first anatomical structure and a second anatomical structure, the surgical guide system comprising:
  a first component comprising a distal end and a proximal end and comprising a palpating portion and a non-palpating portion disposed on an opposing side from the palpating portion, the palpating portion comprising a first ring defining the distal end, a second ring defining the proximal end, and an opening defined along the palpating portion between the first and second rings, the first component defining a channel extending therethrough;
  a second component attached to the non-palpating portion of the first component, the second component defining a guide channel extending therethrough; and
  a guide member slidably disposed in the guide channel; the guide member adapted to be placed at a target site between the first anatomical structure and the second anatomical structure;
  wherein the channel of the first component is adapted to receive a finger of a surgeon such that the finger extends outward from the distal end of the first component and such that the finger is disposed between the palpating portion and the non-palpating portion of the first component and such that the palpating portion is disposed adjacent the first anatomical structure and the non-palpating portion is disposed adjacent the second anatomical structure.

8. A surgical guide system as recited in claim 7 wherein the guide member comprises a guide pin comprising a sharpened distal end configured for piercing the target site.

9. A surgical guide system as recited in claim 7 wherein the first component comprises a cylindrical tube.

10. A surgical guide system as recited in claim 7 wherein the second component comprises a cylindrical tube.

11. A surgical guide system as recited in claim 7 wherein the second component is attached to the non-palpating portion of the first component along a length of the first component between the distal end and the proximal end.

12. A surgical guide system as recited in claim 7 wherein the first component comprises a tapered cylindrical tube comprising a distal end and a proximal end and wherein the first component tapers from a larger diameter at the proximal end to a smaller diameter at the distal end.

13. A surgical guide system as recited in claim 7 wherein the second component is integrally formed with the first component along a length of the non-palpating portion of the first component.

\* \* \* \* \*